United States Patent [19]

Fürst et al.

[11] Patent Number: 4,578,475
[45] Date of Patent: Mar. 25, 1986

[54] NOVEL D-HOMOSTEROIDS

[75] Inventors: Andor Fürst, Basel; Marcel Müller, Frenkendorf, both of Switzerland; Ulrich Kerb; Rudolf Wiechert, both of Berlin, Fed. Rep. of Germany

[73] Assignee: Hoffman-La Roche Inc., Nutley, N.J.

[21] Appl. No.: 573,983

[22] Filed: Jan. 26, 1984

[30] Foreign Application Priority Data

Feb. 11, 1983 [CH] Switzerland .......................... 788/83

[51] Int. Cl.⁴ ................. C07D 211/70; C07D 307/94
[52] U.S. Cl. .................... 548/126; 548/369;
548/241; 549/265; 549/330; 549/543; 558/429
[58] Field of Search ...................... 548/126, 548/369,
241; 549/265, 330, 543; 260/464; 424/272,
273, 269, 279, 285, 278, 304, 311, 331

[56] References Cited
U.S. PATENT DOCUMENTS 3,284,505 11/1966 Halden et al. .......................... 549/543
3,920,703 11/1975 Alig et al. .............................. 549/265
4,140,700 2/1979 Fust et al. ............................. 549/265

FOREIGN PATENT DOCUMENTS 52799 6/1982 European Pat. Off.
2516937 10/1975 Fed. Rep. of Germany.
1406106 6/1964 France.
1071124 6/1967 United Kingdom.

Primary Examiner—John Kight
Assistant Examiner—Garnette D. Draper
Attorney, Agent, or Firm—Jon S. Saxe; Bernard S. Leon; George M. Gould

[57] ABSTRACT

The novel D-homosteroids of the formula

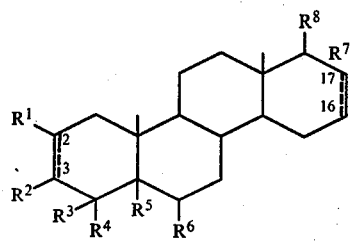

wherein $R^1$ represents a —CN, =NOH or =CH—NHOH group; $R^2$ represents oxo or, where $R^1$ represents a —CN group, $R^2$ represents oxo or a —OAc group; or $R^1$ and $R^2$ together with carbon atoms 2 and 3 of the steroid skeleton represents a [2,3-d]-fused isoxazole ring, a [3,2-c]-fused pyrazole ring, a [3,2-c]-fused N-acylated pyrazole ring or a [2,3-c]-fused furazan ring; Ac represents an acyl group; $R^3$ and $R^4$ represent methyl and $R^5$ and $R^6$ together represent an additional bond between carbon atoms 5 and 6 of the steroid skeleton; or $R^4$ and $R^5$ together represent —O—, $R^3$ represents hydrogen or methyl, and $R^6$ represents hydrogen; $R^7$ represents hydrogen, lower-alkyl or ethynyl; $R^8$ represents hydroxy or acyloxy; or $R^7$ and $R^8$ together represent a spiroether group of the formula

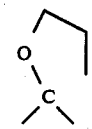

or a spirolactone group of the formula

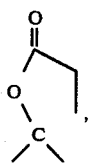

the dotted 16,17-bond is an optional additional carbon-carbon bond; and the dotted 2,3-bond is an additional carbon-carbon bond when $R^1$ and $R^2$ together with carbon atoms 2 and 3 form the isoxazole or pyrazole ring or when $R^2$ represents a —OAc group, inhibit the synthesis of progesterone in organisms and can be used for fertility control. The novel D-homosteroids can be manufactured by molecular modifications of other D-homosteroids.

8 Claims, No Drawings

NOVEL D-HOMOSTEROIDS

The present invention is concerned with novel D-homosteroids of the formula

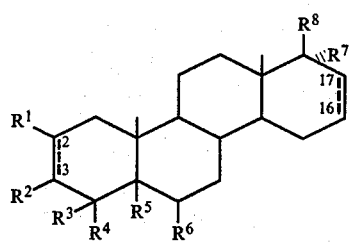

wherein R¹ represents a —CN, =NOH or =CH—N-HOH group; R² represents oxo or, where R¹ represents a —CN group, R² represents oxo or a —OAc group; or R¹ and R² together with carbon atoms 2 and 3 of the steroid skeleton represent a [2,3-d]-fused isoxazole ring, a [3,2-c]-fused pyrazole ring, a [3,2-c]-fused N-acylated pyrazole ring or a [2,3-c]-fused furazan ring; Ac represents an acyl group; R³ and R⁴ represent methyl and R⁵ and R⁶ together represent an additional bond between carbon atoms 5 and 6 of the steroid skeleton; or R⁴ and R⁵ together represent —O—, R³ represents hydrogen or methyl, and R⁶ represents hydrogen; R⁷ represents hydrogen, lower-alkyl or ethynyl; R⁸ represents hydroxy or acyloxy; or R⁷ and R⁸ together represent a spiroether group of the formula

or a spirolactone group of the formula

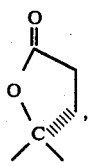

the dotted 16,17-bond is an optional additional carbon-carbon bond; and the dotted 2,3-bond is an additional carbon-carbon bond when R¹ and R² together with carbon atoms 2 and 3 form the isoxazole or pyrazole ring or when R² represents a —OAc group.

The invention is also concerned with pharmaceutical preparations which contain the aforementioned D-homosteroids as the active substance and with a process for the manufacture of these D-homosteroids. Further, the invention is concerned with the D-homosteroids of formula I for use as pharmaceutically active substances, especially as interceptives.

The term "acyl" denotes acyl groups derived from an aliphatic, cycloaliphatic, aromatic, araliphatic and heterocyclic carboxylic acid. Aliphatic carboxylic acids can be saturated or unsaturated. Examples of these acids are especially alkanecarboxylic acids, preferably lower alkanecarboxylic acids such as acetic acid, propionic acid, butyric acid, pivalic acid and caproic acid. Examples of cycloaliphatic carboxylic acids are cyclopentylpropionic acid and cyclohexylpropionic acid. Examples of aromatic carboxylic acids are benzoic acid and substituted benzoic acids such as p-nitrobenzoic acid or toluic acids. Examples of araliphatic carboxylic acids are phenylacetic acid and phenylpropionic acid. Examples of heterocyclic carboxylic acids are N- or S-heterocyclic carboxylic acids which preferably have a 5- or 6-membered ring such as nicotinic acids and thiophenecarboxylic acids. The term "lower" denotes groups containing up to 6 carbon atoms. Alkyl groups can be straight-chain or branched-chain. Examples of such groups are methyl, ethyl, propyl, isopropyl, n-butyl and isomers thereof.

The D-homosteroids of formula I in which R¹ represents cyano and R² represents oxo can be present in tautomeric forms, namely in the form of the 2α-cyano-3-ketone or in enolized form as the 2-cyano-3-hydroxy-Δ²-tautomers. Where R⁴ and R⁵ together represent oxido (—O—), the oxido group must have the α-configuration.

The preferred D-homosteroids of formula I are the 16,17-unsaturated D-homosteroids. Furthermore, D-homosteroids of formula I in which R¹ represents cyano are preferred. 17aβ-Hydroxy-4,4,17a-trimethyl-3-oxo-D-homoandrosta-5,16-diene-2a-carbonitrile is especially preferred.

The D-homosteroids of formula I can be manufactured in accordance with the invention by (a) reacting a D-homosteroid of the formula

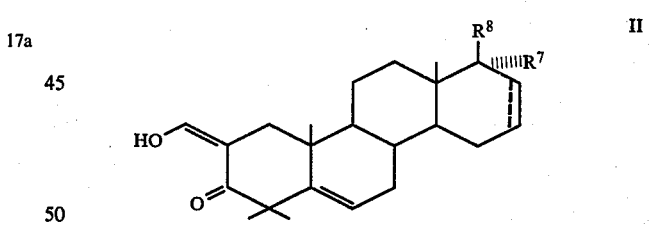

with hydroxylamine or hydrazine or O,N-bis-(trifluoroacetyl)-hydroxylamine; or (b) reacting a D-homosteroid of the formula

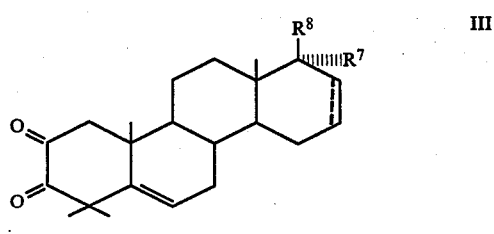

with hydroxylamine; or (c) treating a D-homosteroid of the formula

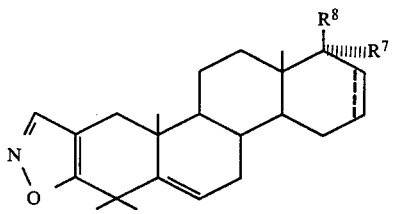

with a strong base; or (d) reacting a D-homosteroid of the formula

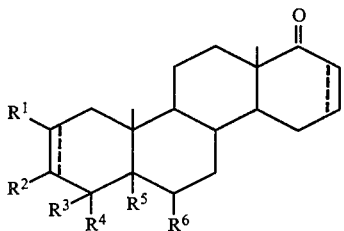

with a metal-organic compound yielding the group $R^7$; or (e) treating a D-homosteroid of the formula

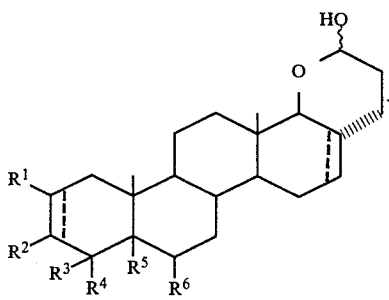

with an oxidation agent; or (f) treating a D-homosteroid of formula I in which $R^1$ represents cyano and $R^2$ represents oxo or $R^1$ and $R^2$ together with carbon atoms 2 and 3 of the steroid skeleton represent a pyrazole ring and/or $R^8$ represents hydroxy; with an acylating agent, or (g) treating a D-homosteroid of the formula

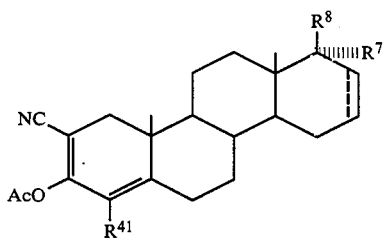

with an oxidation agent and, if desired, treating the 4,5-oxide obtained with a base;

whereby in the foregoing formulae II–VII Ac represents an acyl group; $R^{41}$ represents hydrogen or methyl and $R^1$–$R^8$ have the significance given above.

The reaction of D-homosteroids of formula II in accordance with process variant (a) can be carried out in a manner known per se; for example, in an inert organic solvent such as ethanol or acetic acid while heating. The reaction with hydrazine yields steroid [3,2-c]pyrazoles of the formula

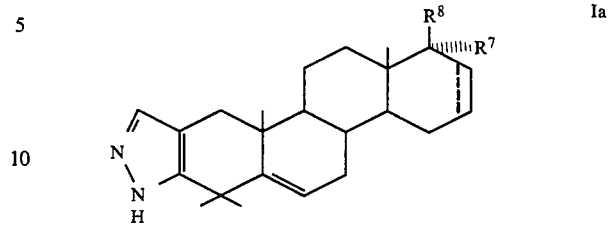

wherein $R^7$ and $R^8$ have the above significance.

The reaction with hydroxylamine yields steroid [2,3-d]isoxaloles of the formula

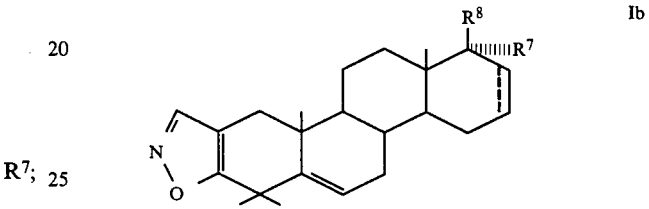

wherein $R^7$ and $R^8$ have the above significance.

The reaction with O,N-bis-(trifluoroacetyl)-hydroxylamine in the presence of a base such as pyridine yields 2-cyano derivatives of the formula

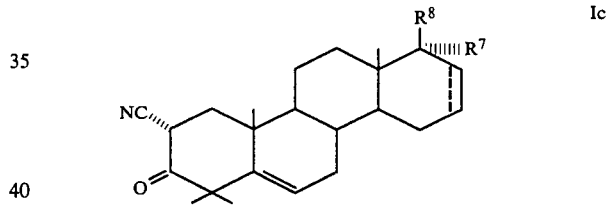

wherein $R^7$ and $R^8$ have the above significance, or enols thereof.

The reaction of a D-homosteroid of formula III with hydroxylamine in accordance with process variant (b) can be carried out in analogy to the reaction of a D-homosteroid of formula II with hydroxylamine. There are thus obtained steroid [2,3-c]furazans of the formula

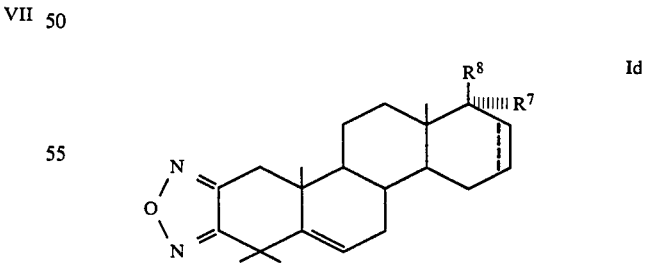

wherein $R^7$ and $R^8$ have the above significance.

In accordance with process variant (c) a D-homosteroid of formula IV is treated with a strong base such as an alkali metal alcoholate (e.g. sodium methylate), preferably at room temperature. This process variant leads to D-homosteroids of formula Ic.

Process variant (d) leads to D-homosteroids of formula I in which $R^8$ represents hydroxy and $R^7$ represents lower-alkyl or ethynyl. Examples of metal-organic compounds which can be reacted with a D-homosteroid of formula V are lower alkyl-magnesium halides and alkali metal alkyls such as methyl lithium and alkali metal acetylides such as sodium, potassium or lithium acetylide. The reaction of a D-homosteroid of formula V with these reagents can be carried out in a manner known per se for reactions of carbonyl compounds with Grignard compounds and alkali metal-organic compounds.

The oxidation of a D-homosteroid of formula VI in accordance with process variant (e) to give a D-homosteroid of formula I in which $R^7$ and $R^8$ represent a spirolactone ring can be carried out in a manner known per se with oxidation agents such as Jones' reagent ($CrO_3H_2SO_4$).

A D-homosteroid of formula Ia or Ic can be converted by treatment with an acylating agent in accordance with process variant (f) into a D-homosteroid of formula Ie or If

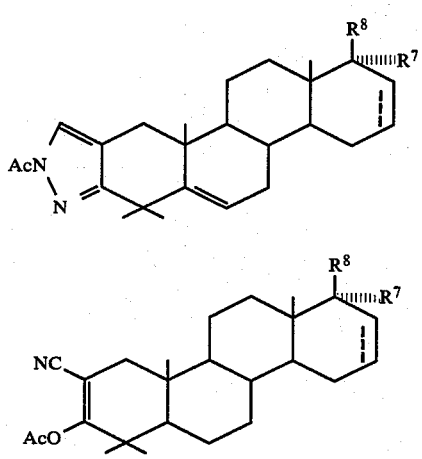

wherein Ac represents acyl and $R^7$ and $R^8$ have the above significance.

Examples of acylating agents are acid anhydrides (e.g. lower-alkanecarboxylic acid anhydrides such as acetic anhydride) and halides (e.g. acetyl chloride). This reaction can be carried out under reaction conditions which are known per se for acylations.

The oxidation of a D-homosteroid of formula VII to give a 4,5-oxide [process variant (g)] can be carried out with an oxidation agent such as a peracid (e.g. perbenzoic acid or peracetic acid). There is thus obtained a D-homosteroid of the formula

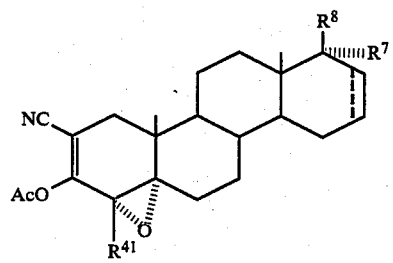

wherein $R^{41}$, $R^7$, $R^8$ and Ac have the above significance.

Treatment of a D-homosteroid of formula Ig with a base such as an aqueous-alcoholic alkali hydroxide or carbonate leads to cleavage of the acyl group Ac and formation of the corresponding 3-ketone.

The D-homosteroids of formula I are pharmacologically active. They act as inhibitors of $\Delta^5$-isomerase/$3\beta$-hydroxysteroid dehydrogenase or of the synthesis of progesterone by the body. Such inhibitors lead to a termination of pregnancy in the early stage [Fertility and Sterility 30 (1978) 86–90].

The activity of the D-homosteroids of formula I as inhibitors of $\Delta^5$-isomerase/$3\beta$-hydroxysteroid dehydrogenase was determined in the following experimental procedures:

in vitro:

Rat overies were homogenized in 0.05 M $Na_2HPO_4$ buffer (pH 7.2) which contained 0.25 M sucrose and 0.05 M dithiothreitol. The microsomes obtained after centrifugation were suspended in 0.05 M $Na_2HPO_4$ buffer (pH 7.4) which contained 0.001 M EDTA. This microsome preparation was assayed firstly for enzymatic activity by measuring the increase of the optical density at 340 nm by the reduction of $NAD^+$. Thereafter, aliquot portions (0.5 μg of protein) were incubated in 1.8 ml of buffer for 30 minutes at 37° C. with 250 pmol of $^{14}C$-pregnelonone, 0.4 mg of $NAD^+$ and different concentrations of the test substance dissolved in the minimum amounts of dimethyl sulphoxide. The reaction was interrupted by the addition of methylene chloride. After extraction and evaporation of the solvent, the radioactive metabolites were separated on silica gel-aluminium plates with benzene/acetone (85:15). The radioactivity was measured by means of a scintillation counter.

in vivo:

Female albino rats were kept under controlled conditions, the synchronicity of the cycle being monitored by daily vaginal douching and subsequent cytological investigation. At proestrus the animals were brought together with male, fertile rats. The successful insemination was checked on the following morning and this day was denoted as the 1st day of the pregnancy. The pregnant animals then received the test substances as a suspension in a standard vehicle (0.5% carboxymethylcellulose, 0.4% TWEEN 80, 0.9% benzyl alcohol and 0.9% NaCl in water) orally or intramuscularly on the 10th day. The animals were killed on the 15th day. The blood was collected and the uteri were investigated for living foetuses, resorptions and vacant implantation positions. The serum hormone concentrations were determined radio-immunologically. The results are compiled in the following Tables.

TABLE 1

| Inhibition of the formation of progesterone in vitro | |
|---|---|
| D-Homosteroid of Example | $IC_{50}$ [nM] |
| 5 | 0.8 |
| 6 | 0.4 |
| 7 | 6 |
| 12 | 6 |
| 17 | 6.5 |
| 22 | 0.9 |
| 25 | 7 |

$IC_{50}$: concentration of the test substance at which the enzyme activity amounts to 50% of the maximum value.

TABLE 2

| D-Homosteroid of Example No. | Dosage (mg/kg) | Interceptive activity in rats | | | | | | | |
|---|---|---|---|---|---|---|---|---|---|
| | | | Serum progesterone (ng/ml) | Living foetuses | | Resorption | | Vacant implantation positions | |
| | | n | 3 h later | n | x | n | x | n | x |
| Vehicle | — | 45 | 105 | 45 | 12 | 25 | 2 | 0 | — |
| 2 | 3.75 | 6 | 87 | 3 | 12 | 2 | 9 | 2 | 13 |
| 2 | 7.5 | 6 | 39 | 0 | — | 0 | — | 6 | 13 |
| 2 | 15 | 6 | 35 | 0 | — | 0 | — | 6 | 12 |
| 3 | 7.5 | 7 | 25 | 4 | 9 | 5 | 6 | 2 | 3 |
| 3 | 15 | 8 | 29 | 4 | 9 | 6 | 3 | 3 | 13 |
| 14 | 7.5 | 7 | 20 | 1 | 3 | 3 | 12 | 4 | 12 |
| 14 | 15 | 8 | 20 | 1 | 12 | 3 | 14 | 4 | 13 |
| 17 | 3.75 | 6 | 32 | 2 | 5 | 5 | 11 | 1 | 13 |
| 17 | 7.5 | 6 | 29 | 0 | — | 2 | 15 | 4 | 11 |
| 19 | 15 | 8 | 9 | 0 | — | 0 | — | 8 | 13 |
| 21 | 7.5 | 7 | 24 | 3 | 6 | 6 | 10 | 2 | 10 |
| 21 | 15 | 7 | 17 | 1 | 15 | 0 | — | 6 | 13 | n: numbers of animals,
x: mean of the observations.

The D-homosteroids of formula I can be used as interceptives in fertility control. The D-homosteroids of formula I can be administered orally or parenterally in the form of pharmaceutical preparations. The dosage of the active substance can amount to about 0.2–4 mg/kg in the case of oral administration depending on its strength of activity. The pharmaceutical preparations can be made up in solid form (e.g. as tablets, dragées, capsules or suppositories) or in liquid form (e.g. as solutions) and can contain a compound of formula I together with an inert inorganic or organic carrier material which is customary per se in such preparations such as water, gelatine, lactose, starch, magnesium sulphate, talc, polyalkylene glycols or alcohols.

The following Examples illustrate the present invention:

EXAMPLE 1

To a solution of 1.0 g of 17aβ-hydroxy-4,4-dimethyl-D-homo-androsta-5,16-dien-3-one in 60 ml of benzene are added while stirring 0.92 g of sodium methylate and subsequently within 5 minutes 2.6 ml of ethyl formate. The mixture is stirred at room temperature for 4 hours, then poured on to ice-water and acidified with concentrated hydrochloric acid. The mixture is extracted three times with ether, washed with water, dried over sodium sulphate and the solvent is evaporated in vacuo. There are obtained 1.1 g of colourless crystals which are heated to 80° C. for 1 hour while stirring with 250 mg of hydroxylamine hydrochloride, 250 mg of sodium acetate and 30 ml of acetic acid. The mixture is poured on to ice-water and extracted with benzene. The organic extract is washed with sodium hydrogen carbonate solution and water, dried over sodium sulphate and the solvent is evaporated in vacuo. The crude crystals are recrystallized from acetone/hexane and there are obtained 850 mg of pure 4,4-dimethyl-D-homo-androsta-2,5,16-trieno-[2,3-d]isoxazol-17aβ-ol of melting point 200°–201° C. $[\alpha]_D^{20} = -99°$ (c=1.0 in dioxan). $\epsilon_{228} = 5710$.

The starting material is prepared as follows:

A solution of 12.0 g of 17aβ-hydroxy-D-homo-androsta-4,16-dien-3-one in 350 ml of tert.butanol is treated under argon with 13.4 g of potassium tert.butylate. Subsequently, 17 ml of methyl iodide are added dropwise and the mixture is heated under reflux for 1 hour. For the working-up, the mixture is poured on to ice-water, extracted with ethyl acetate, the organic extract is washed with water, dried over sodium sulphate and evaporated in vacuo. The residue is chromatographed on silica gel. Elution with methylene chloride/acetone (98:2) gives 8.9 g of pure 17aβ-hydroxy-4,4-dimethyl-D-homo-androsta-5,16-dien-3-one of melting point 217°–219° C. (from acetone/hexane).

EXAMPLE 2

In accordance with Example 1, from 17aβ-hydroxy-4,4,17a-trimethyl-D-homo-androsta-5,16-dien-3-one there was manufactured 4,4,17a-trimethyl-D-homo-androsta-2,5,16-trieno[2,3-d]isoxazol-17aβ-ol of melting point 190°–191° C. (from acetone/hexane). $[\alpha]_D^{20} = 150°$ (c=1.0 in dioxan). $\epsilon_{229} = 5770$.

The starting material was obtained analogously to Example 1 from 17aβ-hydroxy-17a-methyl-D-homo-androsta-4,16-dien-3-one. M.p. 232°–235° C.

EXAMPLE 3

In accordance with Example 1, from 17aβ-hydroxy-4,4,17a-trimethyl-D-homo-androst-5-en-3-one there was manufactured 4,4,17a-trimethyl-D-homo-androsta-2,5-dieno[2,3-d]isoxazol-17aβ-ol of melting point 210°–212° C. (from acetone/hexane). $[\alpha]_D^{20} = -70°$ (c=1.0 in dioxan). $\epsilon_{228} = 5820$.

The starting material was prepared analogously to Example 1 from 17aβ-hydroxy-17a-methyl-D-homo-androst-4-en-3-one. M.p. 212°–214° C.

EXAMPLE 4

Dry acetylene is passed through 50 ml of tetrahydrofuran, cooled to −70° C., for 1 hour. There are then added 15 ml of 2N butyl lithium solution (in hexane) and there is subsequently added dropwise while stirring a solution of 1.75 g of 4,4-dimethyl-D-homo-androsta-2,5,16-trieno[2,3-d]-isoxazol-17a-one in 70 ml of tetrahydrofuran. The mixture is stirred at −50°to −40° C. for 5 hours and then treated slowly with 6 ml of saturated ammonium chloride solution. After leaving to warm to room temperature, the solution is dried over sodium sulphate, filtered and the filtrate is evaporated in vacuo. The residue is recrystallized from acetone/hexane. There is obtained pure 4,4-dimethyl-D-homopregna-2,5,16-trien-20-yno[2,3-d]-isoxazol-17aβ-ol of melting point 253°–256° C. $[\alpha]_D^{20} = 277°$ (c=1.0 in dioxan).

The starting material was prepared as follows:

10.5 g of 4,4-dimethyl-D-homo-androsta-2,5,16-trieno[2,3-d]isoxazol-17aβ-ol (see Example 1) dissolved in 500 ml of acetone are treated at 0° C. within 5 minutes with 8.8 ml of CrO$_3$ solution (Jones'reagent). After 10 minutes, 10 ml of propanol are added, the mixture is poured on to ice-water and extracted with methylene chloride. The organic extract is washed with water, dried over sodium sulphate and evaporated in vacuo. The crude product is recrystallized from acetone/hexane. There are obtained 9.1 g of pure 4,4-dimethyl-D-homo-androsta-2,5,16-trieno[2,3-d]isoxazol-17a-one of melting point 190°–192° C.

EXAMPLE 5

3.5 g of 2-hydroxymethylene-17aβ-hydroxy-4,4-dimethyl-D-homo-androsta-5,16-dien-3-one (see Example 1) and 1.0 g of hydrazine hydrate were heated under reflux for 1 hour in 50 ml of ethanol. The mixture was evaporated to dryness in vacuo. The residue was recrystallized from ether. There were obtained 2.4 g of pure 4,4-dimethyl-2'H-D-homo-androsta-2,5,16-trieno[3,2-c]pyrazol-17aβ-ol of melting point 169°–170° C. $[a]_D^{20} = -80°$ (c=0.5 in dioxan). $\epsilon_{222}=4950$.

EXAMPLE 6

3.85 ml of an about 2 molar methyl lithium solution are added within 10 minutes to a solution, cooled to 0° C., of 1.55 g of 4,4-dimethyl-2'H-D-homo-androsta-2,5,16-trieno-[3,2-c]pyrazol-17a-one in 40 ml of absolute tetrahydrofuran and 40 ml of absolute ether. After stirring at 0° C. for 2 hours, the mixture is treated with 5 ml of sodium sulphate solution, then poured on to ice-water and extracted with methylene chloride. The organic extract is washed with water, dried over sodium sulphate and evaporated in vacuo. The crude product is chromatographed on silica gel. Elution with methylene chloride/acetone (9:1) yields 700 mg of pure 4,4,17a-trimethyl-2'H-D-homo-androsta-2,5,16-trieno[3,2-c]-pyrazol-17aβ-ol of melting point 268°–270° C. $[a]_D^{20} = -133°$ (c=0.5 in dioxan). $\epsilon_{223}=5060$.

The starting material is prepared as follows:

4.1 ml of Jones' reagent are added within 10 minutes to a solution, cooled to −20° C., of 4.8 g of 4,4-dimethyl-2'H-D-homo-androsta-2,5,16-trieno[3,2-c]pyrazol-17aβ-ol in 190 ml of acetone. Usual working-up gives, after chromatography on silica gel, pure 4,4-dimethyl-2'H-D-homo-androsta-2,5,16-trieno[3,2-c]pyrazol-17a-one of melting point 287°–288°.

EXAMPLE 7

In accordance with Example 6, but using butyl lithium in place of methyl lithium, from 4,4-dimethyl-2'H-D-homo-androsta-2,5,16-trieno[3,2-c]pyrazol-17a-one there is obtained pure 17a-butyl-4,4-dimethyl-2'H-D-homo-androsta-2,5,16-trieno[3,2-c]pyrazol-17aβ-ol of melting point 196°–198° C. (from ether). $[a]_D^{20} = -151°$ (c=0.3 in dioxan). $\epsilon_{223}=5230$.

EXAMPLE 8

In accordance with Example 6, but using butyl lithium in place of methyl lithium, from 4,4-dimethyl-D-homo-androsta-2,5,16-trieno[2,3-d]isoxazol-17a-one there is obtained pure 17a-butyl-4,4-dimethyl-D-homo-androsta-2,5,16-trieno[2,3-d]isoxazol-17aβ-ol in amorphous form. $[a]_D^{20} = -574°$ (c=0.066 in dioxan). $\epsilon_{226}=7000$.

EXAMPLE 9

In accordance with Example 4, from 4,4-dimethyl-2'H-D-homo-androsta-2,5,16-trieno[3,2-c]pyrazol-17a-one there is obtained pure 4,4-dimethyl-2'H-D-homo-17aα-pregna-2,5,16-trien-20-yno[3,2-c]pyrazol-17a-ol of melting point 269°–271° C. (from acetone). $[a]_D^{20} = -257°$ (c=0.1 in dioxan). $\epsilon_{222}=5770$.

EXAMPLE 10

In accordance with Example 1, from 4,5-dihydro-4',4'-dimethylspiro[furan-2(3H),17'a(beta 1)-D-homo-androsta-[5,16]dien]-3-one there is obtained pure 4,5-dihydro-4',4'-dimethylspiro[furan-2(3H),17'a(beta 1)-D-homo-androsta[2,5,16]trieno[2,3-d]isoxazole]of melting point 196°–197° C. (from acetone/hexane). $[a]_D^{20} = +165°$ (c=0.9 in dioxan). $\epsilon_{228}=5890$.

The starting material is prepared in accordance with Example 1 by methylating 4,5-dihydro-spiro[furan-2(3H),17'a-(beta 1)-D-homo-androsta[4,16]dien]-3'-one. M.p. 140°–142° C. $[a]_D^{20} = -131°$ (c=0.5 in dioxan).

EXAMPLE 11

A mixture of 1.0 g of 17β-hydroxy-4,4,17-trimethyl-D-homo-androsta-5,16-diene-2,3-dione, 1.0 g of hydroxylamine hydrochloride and 50 ml of pyridine was heated to 100° C. for 6 hours. The mixture was evaporated in vacuo, the residue was dissolved in methylene chloride and the methylene chloride solution was washed successively with ice cold dilute hydrochloric acid, water, saturated sodium hydrogen carbonate solution and water and then dried over sodium sulphate. After evaporation of the solvent, there was obtained 1.0 g of crystalline dioxan which was heated to 160° C. for 90 minutes with 50 ml of ethylene gylcol and 2.0 g of potassium hydroxide. The mixture was poured on to ice-water, acidified with hydrochloric acid and extracted with methylene chloride. The organic extract was washed with water, dried over sodium sulphate and evaporated. By recrystallization from acetone/hexane there was obtained 0.8 g of pure 4,4,17a-trimethyl-D-homo-androsta-5,16-dieno[2,3-d]furazan-17β-ol of melting point 178°–180° C. $[a]_D^{25} = -137°$ (c=0.4 in dioxan). $\epsilon_{215}=5640$.

The starting material was prepared as follows:

10 g of 17aβ-hydroxy-4,4,17a-trimethyl-D-homo-androsta-5,16-dien-3-one and 15 g of potassium tert.butylate were dissolved in 600 ml of tert.butanol and heated to 70° C. Air was conducted through the solution while stirring for 2.5 hours. For the working-up, the mixture was poured on to ice-water, acidified with acetic acid and extracted with methylene chloride. The organic extract was washed with water, dried over sodium sulphate and evaporated in vacuo. The residue was chromatographed on silica gel with hexane/acetane (9:1) and yielded 6.5 g of pure 17β-hydroxy-4,4,17-trimethyl-D-homo-androsta-5,16-diene-2,3-dione of melting point 155°–157° C.

EXAMPLE 12

1.5 ml of acetic acid anhydride are added dropwise to a solution, cooled to −15° C., of 150 mg of 4,4-dimethyl-2'H-D-homo-androsta-2,5,16-trieno[3,2-c]pyrazol-17aβ-ol and 50 mg of 4-dimethylaminopyridine in 1.5 ml of triethylamine. The mixture is stirred at −15° C. for 90 minutes, then poured on to ice-water and extracted with methylene chloride. The organic phase is washed with water, dried over sodium sulphate and evaporated in vacuo. The crude product is chromatographed on 10 g of silica gel. Elution with methylene chloride/acetone (99:1) yields 160 mg of pure amorphous 1'-acetyl-4,4-dimethyl-1'H-D-homo-androsta-5,16-dieno[3,2- c]pyrazol-17aβ-yl acetate. [a]$_D^{20}$= −63° (c=0.4 in dioxan). $\epsilon_{253}$=19320.

EXAMPLE 13

In accordance with Example 12, from 4,4-dimethyl-2′H-D-homo-17aα-pregna-2,5,16-trien-20-yno[3,2-c]pyrazol17a-ol (see Example 9) there is obtained pure 1′-acetyl-4,4-dimethyl-1′H-D-homo-17aα-pregna-5,16-dien-20-yno[3,2c]-pyrazol-17a-ol of melting point 238°–240° C. [a]$_D^{20}$= −240° (c=0.3 in dioxan). $\epsilon_{257}$=19100.

EXAMPLE 14

A mixture of 900 mg of 17aβ-hydroxy-4,4,17a-trimethyl-D-homo-androsta-2,5-dieno[2,3-d]isoxazol-17aβ-ol, 100 ml of absolute ether, 1 ml of methanol and 210 ml of sodium ethylate is stirred at room temperature for 5 hours. For the working-up, the mixture is poured on to ice-water, acidified with dilute hydrochloric acid and extracted with ether. The ether extract is washed with water, dried over sodium sulphate and evaporated in vacuo. The crude product is recrystallized from ether and there are obtained 650 mg of pure 17aβ-hydroxy-4,4,17a-trimethyl-3-oxo-D-homo-androst-5-ene-2a-carbonitrile of melting point 196°–197° C. ]a]$_D^{20}$= −34° (c=1.0 in dioxan). $\epsilon_{236}$=7800.

EXAMPLE 15

In accordance with Example 14, from 4,4-dimethyl-D-homo-17aα-pregna-2,5,16-trien-20-yno[3,2-d]isoxazol-17a-ol there is obtained pure 17a-hydroxy-4,4-dimethyl-3-oxo-D-homo-17aα-pregna-5,16-dien-20-yne-2a-carbonitrile of melting point 241°–244° C. (from acetone/hexane). [a]$_D^{20}$= −25° (c=1.0 in dioxan). $\epsilon_{237}$=7600.

EXAMPLE 16

In accordance with Example 14, from 4,5-dihydro-4′,4′-dimethyl-spiro[furan-2(3H),17′a-(beta 1)-D-homo-androsta-[2,5,16]trieno[2,3-d]isoxazole] there is obtained pure 4,5-dihydro-4′,4′-dimethyl-3′-oxo-spiro[furan-2(3H),17′a(beta 1)-D-homo-androsta[5,16]diene]-2a-carbonitrile of melting point 158°–160° C. [a]$_D^{20}$= −139° (c=0.3 in dioxan). $\epsilon_{238}$=7400.

EXAMPLE 17

A solution of 65 g of 2-hydroxymethylene-17aβ-hydroxy-4,4,17a-trimethyl-D-homo-androsta-5,16-dien-3-one and 84 g of O,N-bis(trifluoroacetyl)-hydroxylamine in 1800 ml of benzene and 180 ml of pyridine is heated to boiling for 4 hours under argon. For the working-up, the mixture is poured on to ice-water and extracted with benzene. The benzene solution is washed with water, dried over sodium sulphate and the solvent is evaporated in vacuo. The residue is chromatographed on 2 kg of silica gel. Elution with hexane/acetone (9:1) yields firstly 5.9 g of 4,4,17a-trimethyl-D-homo-androsta-2,5,16-trieno[2,3-d]isoxazol-17aβ-ol (see Example 2) and subsequently 34 g of pure 17aβ-hydroxy-4,4,17a-trimethyl-3-oxo-D-homo-androsta-5,16-diene-2α-carbonitrile of melting point 178°–180° C. (from ether). [a]$_D^{20}$ = −121° (c=0.3 in dioxan). $\epsilon_{237}$=6950.

EXAMPLE 18

A solution of 200 mg of 17aβ-hydroxy-4,4,17a-trimethyl-3-oxo-D-homo-androsta-5,16-diene-2α-carbonitrile in 5 ml of pyridine and 5 ml of acetic anhydride is held at room temperature for 2 hours. For the working-up, the mixture is poured on to ice-water and extracted with methylene chloride. The organic extract is washed with water, dried over sodium sulphate and evaporated in vacuo. The residue is recrystallized from acetone/hexane. There are obtained 170 mg of pure 3-acetoxy-17aβ-hydroxy-4,4,17a-trimethyl-D-homo-androsta-2,5,16-triene-2-carbonitrile of melting point 184°–186° C. [α]$_D$20= −141° (c=0.5 in dioxan). $\epsilon_{217}$=9700.

EXAMPLE 19

400 mg of lithium in small pieces are added to a solution, cooled to −30° C., of 1.75 g of 4,4-dimethyl-D-homo-androsta-2,5,16-trieno[2,3-d]isoxazol-17a-one in 50 ml of absolute tetrahydrofuran. Thereafter, 4.0 g of 3-bromopropionaldehyde dimethyl acetal are added dropwise at −30° C. within 40 minutes. The mixture is then stirred at −30° C. for a further 1 hour and at 0° C. for 1 hour. For the working-up, excess lithium is filtered off and the filtrate is poured on to ice-water and extracted with ethyl acetate. The organic extract is washed with water, dried over sodium sulphate and evaporated in vacuo. There are obtained 2.6 g of yellow amorphous product which is dissolved in 100 ml of acetic acid and 20 ml of water and stirred at room temperature for 2 hours. The mixture is then poured on to ice-water and extracted with ethyl acetate. The extract is washed with sodium carbonate solution and water, dried over sodium sulphate and evaporated in vacuo. There are obtained 2.20 g of amorphous lactol which is dissolved in 50 ml of methylene chloride and 50 ml of acetone and treated with 1.90 ml of Jones' reagent. The mixture is stirred at 15° C. for 40 minutes, then treated with 2 ml of 2-propanol and subsequently poured on to ice-sodium chloride solution. The mixture is extracted with methylene chloride, the organic extract is washed with water, dried over sodium sulphate and evaporated in vacuo. There are obtained 2.1 g of crude product which is chromatographed on 100 g of silica gel. Elution with methylene chloride/acetone (99:1) yields 940 mg of pure 2α-cyano-4,4-dimethyl-3-oxo-D-homo-17aα-pregna-5,16-diene-21,17a-carbolactone of melting point 203°–205° C. [α]$_D^{20}$= −114° (c=0.5 in dioxan). $\epsilon_{238}$=6950.

EXAMPLE 20

0.48 ml of tert.butyl nitrite is added to a solution of 1.0 g of 17aβ-hydroxy-4,4,17a-trimethyl-D-homo-androsta-5,16-dien-3-one and 330 mg of potassium tert.butylate in 60 ml of tert.butanol. The mixture is stirred at 60° C. under argon for 5 hours. For the working-up, the mixture is concentrated in vacuo, the residue is taken up in methylene chloride, the methylene chloride solution is washed with water, dried over sodium sulphate and evaporated in vacuo. There is obtained 1.0 g of crude product which, after chromatography on silica gel [hexane/acetone (7:1)], yields 850 mg of pure 17aβ-hydroxy-4,4,17a-trimethyl-D-homo-androsta-5,16-diene-2,3-dione-2-oxime of melting point 248° C. [α]$_D^{20}$= −6° (c=0.2 in dioxan). $\epsilon_{237}$=8100.

EXAMPLE 21

A mixture of 370 mg of 17aβ-hydroxy-4,4,17a-trimethyl-D-homo-androsta-5,16-dien-3-one, 83 mg of hydroxylamine hydrochloride, 98 mg of sodium acetate and 10 ml of dimethyl sulphoxide was stirred at room temperature for 96 hours under argon. For the working-up, the mixture was poured on to ice-water and extracted with benzene. The benzene extract was washed with water, dried over sodium sulphate and evaporated in vacuo. The residue was chromatographed on 20 g of silica gel. Elution with hexane/acetone (8:1) yielded 157 mg of pure 17aβ-hydroxy-2-[(hydroxyamino)methylene]-4,4,17a-trimethyl-D-homo-androsta-5,16-dien-3-one of melting point 156°–160° C. $[\alpha]_D^{25} = -10°$ (c=0.5 in dioxan). $\epsilon_{285} = 4500$.

EXAMPLE 22

740 mg of m-chloroperbenzoic acid are added to a solution, cooled to 0° C, of 3,17aβ-diacetoxy-2-cyano-D-homo-androsta-2,4,16-triene in 100 ml of ether. The mixture is stirred at room temperature for 22 hours and then treated with a further 470 mg of m-chloroperbenzoic acid. After a further 8 hours, the mixture is poured on to a mixture of ice, water and sodium bicarbonate solution and extracted with ether. The ether extract is washed with water, dried over sodium sulphate and evaporated in vacuo. The crude product is recrystalized from acetone/hexane. There is obtained 1.0 g of pure 3,17aβ-diacetoxy-4α,5α-epoxy-D-homo-5α-androsta-2,16-diene-2-carbonitrile of melting point 218°–220° C. $[\alpha]_D^{20} = +40°$ (c=1.0 in dioxan). $\epsilon_{240} = 9020$.

The starting material is prepared as follows:

17aβ-Hydroxy-D-homo-androsta-4,16-dien-3-one is converted with ethyl formate and sodium hydride into the 2-hydroxymethylene compound which with hydroxylamine hydrochloride in ethanol yields D-homo-androsta-2,4,16-trieno[2,3-d]isoxazol-17aβ-ol of melting point 194°–196° C. This compound is cleaved with sodium methylate in ether and methanol to give 17aβ-hydroxy3-keto-D-homo-androsta-4,16-diene-2α-carbonitrile of melting point 144°–147° C. Acetylation with acetic anhydride in pyridine yields the desired 3,17aβ-diacetoxy-2-cyano-D-homo- androsta-2,4,16-triene.

EXAMPLE 23

A mixture of 500 mg of 3,17aβ-diacetoxy-4α,5α-epoxy-D-homo-5α-androsta-2,16-diene-2-carbonitrile, 500 mg of potassium carbonate, 500 ml of methanol and 5 ml of water is stirred at room temperature for 1 hour under argon. For the working-up, the mixture is poured on to ice-water and extracted with methylene chloride. The organic extract is washed with water, dried over sodium sulphate and evaporated in vacuo. The residue is recrystallized from acetone/hexane. There are obtained 265 mg of pure 17aβ-acetoxy-4α, 5-epoxy-3-oxo-D-homo-5α-androst-16-ene-2α-carbonitrile of melting point 191°–193° C. $[\alpha]_D^{20} = +53°$ (c=0.5 in dioxan). $\epsilon_{254} = 6980$.

EXAMPLE 24

In accordance with Example 22, from 3-acetoxy-17aβ-hydroxy-4,17a-dimethyl-D-homo-androsta-2,4,16-triene-2-carbonitrile there is obtained pure 3-acetoxy-4α,5-epoxy-17aβ-hydroxy-4,17a-dimethyl-D-homo-5α-androsta-2,16-diene-2-carbonitrile of melting point 192°–193° C. (from ether/hexane). $[\alpha]_D^{20} = -3°$ (c=0.3 in dioxan). $\epsilon_{240} = 8460$.

The starting material is prepared as follows:

17aβ-Hydroxy-17aα-methyl-D-homo-androsta-4,16-dien-3-one is methylated with methyl iodide/potassium tert.-butylate to give 17aβ-hydroxy-4,17aα-methyl-D-homo-androsta-4,16 -diene-3-one of melting point 152°–153° C. Reaction with ethyl formate/sodium methylate to give the 2-hydroxymethylene compound and subsequent reaction with O,N-bis-(trifluoroacetyl)-hydroxylamine in accordance with Example 17 yields 17aβ-hydroxy-4,17a-dimethyl-D-homo-androsta-4,16-diene-2α-cartonitrile as an amorphous substance. Reaction with acetic anhydride/pyridine finally yields pure 3-acetoxy-17aβhydroxy-4,17a-dimethyl-D-homo-androsta-2,4,16-triene-2-carbonitrile of melting point 210°–212° C.

EXAMPLE 25

In accordance with Example 23, from 3-acetoxy-4α,5-epoxy-17aβ-hydroxy-4,17a-dimethyl-D-homo-5α-androsta-2,16-diene-2-carbonitrile there was obtained pure 4α, 5-epoxy-17aβ-hydroxy-4,17a-dimethyl-3-oxo-D-homo-5α-androst-16-ene-2α-carbonitrile of melting point 190°–192° C. (from acetone/ hexane). $[\alpha]_D^{20} = -88°$ (c=0.3 in dioxan). $\epsilon_{251} = 4880$.

EXAMPLE A

A tablet for oral administration can contain the following ingredients:

Active substance (e.g. 17aβ-hydroxy-4,4,17a-trimethyl-3-oxo-D-homoandrosta-5,16-diene-2β-carbonitrile) 20 mg
Lactose 120 mg
Maize starch 80 mg
Talc 4 mg
Magnesium stearate 1 mg

We claim:

1. D-Homosteroids of the formula

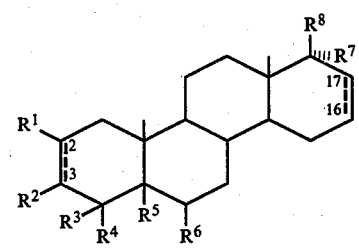

I wherein $R^1$ represents a —CN, =NOH or =CH—N-HOH group; $R^2$ represents oxo or, where $R^1$ represents a —CN group, $R^2$ represents oxo or a —OAc group; or $R^1$ and $R^2$ together with carbon atoms 2 and 3 of the steroid skeleton represent a [2,3-d]-fused isoxazole ring, a [3,2-c]-fused pyrazole ring, a [3,2-c]-fused N-acylated pyrazole ring or a [2,3-c]-fused furazan ring; Ac represents an acyl group: $R^3$ and $R^4$ represent methyl and $R^5$ and $R^6$ together represent an additional bond between carbon atoms 5 and 6 of the steroid skeleton; or $R^4$ and $R^5$ together represent —O—, $R^3$ represents hydrogen or methyl, and $R^6$ represents hydrogen; $R^7$ represents hydrogen, lower-alkyl or ethynyl; $R^8$ represents hydroxy or acyloxy; or $R^7$ and $R^8$ together represent a spiroether group of the formula

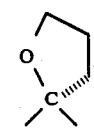

17a or a spirolactone group of the formula

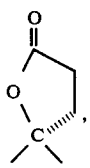

the dotted 16,17-bond is an optional additional carbon-carbon bond; and the dotted 2,3-bond is an additional carbon-carbon bond when $R^1$ and $R^2$ together with carbon atoms 2 and 3 form the isoxazole or pyrazole ring or when $R^2$ represents a —OAc group.

2. In accordance with claim 1, 16,17-Unsaturated D-homosteroids of formula I.

3. In accordance with claim 1, D-homosteroids of formula I, wherein $R^1$ represents cyano.

4. In accordance with claim 1, the compound 17aβ-hydroxy-4,4,17a-trimethyl-3-oxo-D-homo-androsta-5,16-diene-2β-carbonitrile.

5. In accordance with claim 1, D-homosteroids selected from 17aβ-hydroxy-4,4,17a-trimethyl-3-oxo-D-homo-androst-5-ene-2α-carbonitrile, 17a-hydroxy-4,4-dimethyl-3-oxo-D-homo-17aα-pregna-5,16-dien-20-yne-2α-carbonitrile, 4,5-dihydro-4′,4′-dimethyl-3′-oxospiro[furan-2(3H),17′a(beta 1)-D-homo-androsta[5,16]-diene]-2α-carbonitrile, 3-acetoxy-17aα-hydroxy-4,4,17a-trimethyl-D-homo-androsta-2,5,16-triene-2-carbonitrile, 2α-cyano-4,4-dimethyl-3-oxo-D-homo-17aα-pregna-5,16-diene-21,17a-carbolactone, 3,17aβ-diacetoxy-4α,5α-epoxy-D-homo-5α-androsta-2,16-diene-2-carbonitrile, 17aβ-acetoxy-4α,5-epoxy-3-oxo-D-homo-5α-androst-16-ene-2α-carbonitrile, 3-acetoxy-4α,5-epoxy-17aβ-hydroxy-4,17a-dimethyl-D-homo-5α-androsta-2,16-diene-2-carbonitrile and 4α,5-epoxy-17aβ-hydroxy-4,17a-dimethyl-3-oxo-D-homo-5α-androst-16-ene-2α-carbonitrile.

6. In accordance with claim 1, D-homosteroids selected from 4,4-dimethyl-D-homo-androsta-2,5,16-trieno[2,3-d]isoxazol-17aβ-ol, 4,4,17a-trimethyl-D-homo-androsta-2,5,16-trieno[2,3-d]isoxazol-17aβ-ol, 4,4,17a-trimethyl-D-homo-androsta-2,5-dieno[2,3-d]isoxazol-17aβ-ol, 4,4-dimethyl-D-homo-pregna-2,5,16-trien-20-yno[2,3-d]isoxazol-17aβ-ol, 4,4-dimethyl-2′H-D-homo-androsta-2,5,16-trieno[2,3-c]pyrazol-17aβ-ol, 4,4,17a-trimethyl-2′H-D-homo-androsta-2,5,16-trieno[3,2-c]pyrazol-17aβ-ol, 17a-butyl-4,4-dimethyl-2′H-D-homo-androsta-2,5,16-trieno[2,3-c]pyrazol-17aβ-ol, 17a-butyl-4,4-dimethyl-D-homo-androsta-2,5,16-trieno[2,3-d]isoxazol-17aβ-ol, 4,4-dimethyl-2′H-D-homo-17aα-pregna-2,5,16-trieno-20-yno[3,2-c]pyrazol-17a-ol, 4,5-dihydro-4′,4′-dimethylspiro[furan-2(3H),17′a(beta 1)-D-homo-androsta[2,5,16]trieno[2,3-d]isoxazole, 4,4,17a-trimethyl-D-homo-androsta-5,16-dieno[2,3-d]furazan-17β-ol, 4,4-dimethyl-2′H-D-homo-androsta-2,5,16,trieno[3,2-c]pyrazol-17aβ-ol and 1′-acetyl-4,4-dimethyl-1′H-D-homo-17aα-pregna-5,16-dien-20-yno[3,2-c]pyrazol-17a-ol.

7. In accordance with claim 1, D-homosteroids selected from 17aβ-hydroxy-4,4,17a-trimethyl-D-homo-androsta-5,16-dien-2,3-dione-2-oxime and 17aβ-hydroxy-2-[(hydroxyamino)methylene]-4,4,17a-trimethyl-D-homo-androsta-5,16-dien-3-one.

8. A pharmaceutical preparation comprising a D-homosteroid of the formula

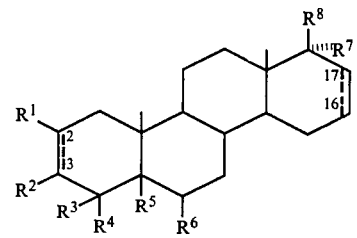

wherein $R^1$ represents a —CN, =NOH or =CH—NHOH group; $R^2$ represents oxo or, where $R^1$ represents a —CN group, $R^2$ represents oxo or a —OAc group; or $R^1$ and $R^2$ together with carbon atoms 2 and 3 of the steroid skeleton represent a [2,3-d]-fused isoxazole ring, a [3,2-c]-fused pyrazole ring, a [3,2-c]-fused N-acylated pyrazole ring or a [2,3-c]-fused furazan ring; Ac represents an acyl group $R^3$ and $R^4$ represent methyl and $R^5$ and $R^6$ together represent an additional bond between carbon atoms 5 and 6 of the steroid skeleton; or $R^4$ and $R^5$ together represent —O—, $R^3$ represents hydrogen or methyl, and $R^6$ represents hydrogen; $R^7$ represents hydrogen, lower-alkyl or ethynyl; $R^8$ represents hydroxy or acyloxy; or $R^7$ and $R^8$ together represent a spiroether group of the formula

or a spirolactone group of the formula

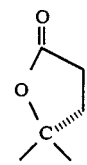

the dotted 16,17-bond is an optional additional carbon-carbon bond; and the dotted 2,3-bond is an additional carbon-carbon bond when $R^2$ and $R^3$ together with carbon atoms 2 and 3 form the isoxazole or pyrazole ring or when $R^2$ represents a —OAc group, and a pharmaceutically effective carrier material.

* * * * *

UNITED STATES PATENT AND TRADEMARK OFFICE
CERTIFICATE OF CORRECTION

PATENT NO. : 4,578,475
DATED : March 25, 1986
INVENTOR(S) : Andor Furst, Marcel Muller, Ulrich Kerb, Rudolf Wiechert It is certified that error appears in the above-identified patent and that said Letters Patent is hereby corrected as shown below:

In claim 6

Column 15, Line 50, " [2,3-c ] should be [3,2-c]

Column 15, Line 53, "triend" should be trien

Column 15, line 47, "[2,3-c]" should read -- [3,2-c] --.

Signed and Sealed this

Second Day of August, 1988

Attest:

DONALD J. QUIGG

Attesting Officer     Commissioner of Patents and Trademarks